(12) United States Patent
Bledsoe

(10) Patent No.: US 7,905,851 B1
(45) Date of Patent: Mar. 15, 2011

(54) PATELLA BRACE

(75) Inventor: Barry P. Bledsoe, Burleson, TX (US)

(73) Assignee: Medical Technology, Inc., Grand Prairie, TX (US)

( * ) Notice: Subject to any disclaimer, the term of this patent is extended or adjusted under 35 U.S.C. 154(b) by 119 days.

(21) Appl. No.: 12/208,758

(22) Filed: Sep. 11, 2008

(51) Int. Cl.
*A61F 5/00* (2006.01)
*A61F 5/24* (2006.01)

(52) U.S. Cl. ... 602/26; 128/95.1; 128/112.1; 128/121.1; 128/123.1

(58) Field of Classification Search ................. 602/1, 5, 602/23, 26; 128/95.1, 112.1, 121.1, 123.1
See application file for complete search history.

(56) References Cited

U.S. PATENT DOCUMENTS

| | | | |
|---|---|---|---|
| 4,928,670 A * | 5/1990 | DeLorenzo | 602/26 |
| 4,991,571 A * | 2/1991 | Kausek | 602/16 |
| 5,277,697 A | 1/1994 | France et al. | |
| 5,792,084 A * | 8/1998 | Wilson et al. | 602/13 |
| 5,797,864 A * | 8/1998 | Taylor | 602/26 |
| 6,213,968 B1 | 4/2001 | Heinz et al. | |
| 6,551,264 B1 * | 4/2003 | Cawley et al. | 602/26 |
| 7,059,329 B2 * | 6/2006 | Mason et al. | 128/861 |
| 7,060,045 B2 | 6/2006 | Mason et al. | |
| 7,083,586 B2 | 8/2006 | Simmons et al. | |
| 2006/0200057 A1 * | 9/2006 | Sterling | 602/5 |
| 2008/0208095 A1 * | 8/2008 | Kazmierczak et al. | 602/26 |

OTHER PUBLICATIONS

Advertisement for Donjoy Tru-Pull (Date Unknown).

* cited by examiner

*Primary Examiner* — Patricia M Bianco
*Assistant Examiner* — Tarla R Patel
(74) *Attorney, Agent, or Firm* — James E. Walton; Richard G. Eldredge

(57) ABSTRACT

A patella brace has two rigid shells, a compression member coupled about the two rigid shells, and two hinge assemblies operatively connecting the two rigid shells for allowing translation, wherein the compression member restrains a joint while the two rigid shells translate about the two hinge assemblies.

17 Claims, 19 Drawing Sheets

PATELLA BRACE

BACKGROUND

1. Field of the Invention

The present application relates to braces and more particularly, knee braces.

2. Description of Related Art

Subluxation is an incomplete or partial dislocation of a joint or organ. Though believed to occur when the leg is in full extension, patellar subluxation generally occurs as the knee bends between 20 and 50 degrees.

To assist in guiding the patella to the correct orientation, an array of devices are employed, from soft elastic knee braces, to structures which couple about the knee in order to restrain the patella in the correct orientation.

While soft elastic knee braces act to compress the knee and provide warmth, they generally provide little support to a user.

Alternatively, more firm structures which couple about the femur and tibia, operate most commonly by employing elastomeric straps or bands which run snugly along the side of the knee. As the knee bends, tension in the straps or bands increases to apply greater pressure towards a patella. Though these types of devices may appear to work, they are not without fault.

In order for the elastomeric straps to function, both while the knee is in full extension and making bending motions, the straps are restrained to a side of the brace while wrapped in tension about the patella. Due to the composition and wrapping orientation of the strap, as the knee bends, offsetting forces are applied towards the patella. When sufficient offsetting forces are applied, combined with a lack of rigid coupling of the brace to the wearer's leg, the brace often rolls from about the femur and tibia, failing to properly secure the patella.

Although the aforementioned devices represent great strides in the area of knee braces, many shortcomings remain.

DESCRIPTION OF THE DRAWINGS

The novel features believed characteristic of the invention are set forth in the appended claims. However, the invention itself, as well as a preferred mode of use, and further objectives and advantages thereof, will best be understood by reference to the following detailed description when read in conjunction with the accompanying drawings, wherein:

DETAILED DESCRIPTION OF THE PREFERRED EMBODIMENT

Figure 1A:
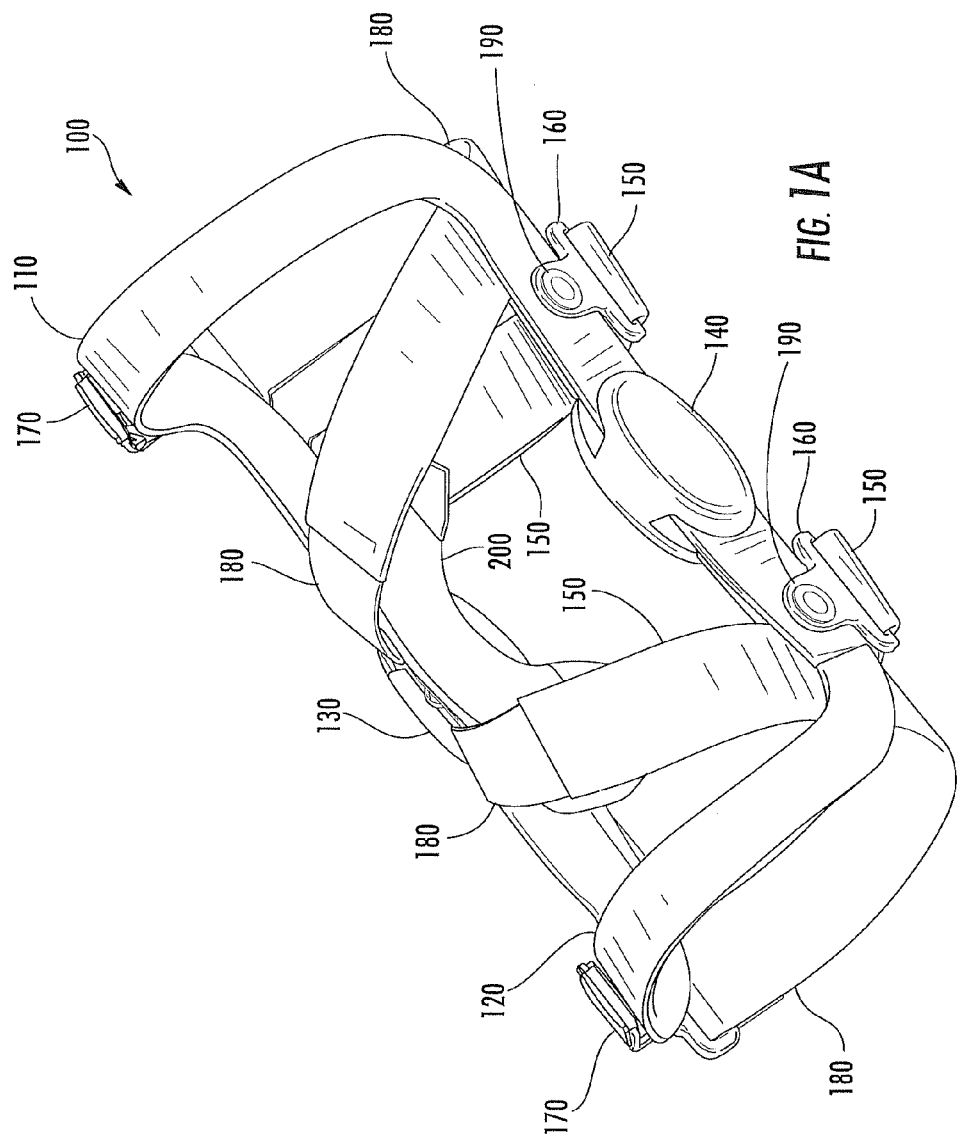
FIG. 1A is an oblique view of a patella brace according to a preferred embodiment of the present application.

Referring to FIG. 1A, there is shown at 100 an oblique view of a patella brace according to a preferred embodiment of the present application. As depicted by a preferred embodiment in the drawings, a patella brace 100 having rigid shells 110 and 120 coupled about hinge assemblies 130 and 140, according to a preferred embodiment of the present application, is illustrated. Compression member 200 couples to hinge assembly 130. Strap restraints 160 and buckles 170 are disposed about the exterior periphery of rigid shells 110 and 120. Straps 150 couple to strap restraints 160. Straps 150 wrap from strap restraints 160 around a user's femur and tibia and secure to another strap restraint 160. Straps 180 connect to buckles 170 and compression member 200. Straps 180 wrap from buckles 170, between padding disposed about the inside of a rigid shells 110 and 120, and fasten to compression member 200. Fasteners 190 couple strap restraints 160 and buckles 170 to rigid shells 110 and 120 to allow strap restraints 160 and buckles 170 to pivot about rigid shells 110 and 120. Portions of straps 150 and straps 180 can be made of hook and pile structures and other fasteners including, but not limited to, buttons, zippers, and snaps to secure various components.

Rigid shells 110 and 120 are anatomically contoured to conform about human appendages to prevent rolling of the patella brace 100. For example, rigid shell 110 has two linearly shaped arms that are spaced parallel to one another and are connected by an arcuate curve. Rigid shell 120 has two linearly shaped arms that are spaced parallel to one another and are connected by an arcuately formed member. In a preferred embodiment, rigid shells 110 and 120 are formed in accordance with the shape of a human femur and tibia in order to prevent the patella brace 100 from rolling.

Figure 1B:
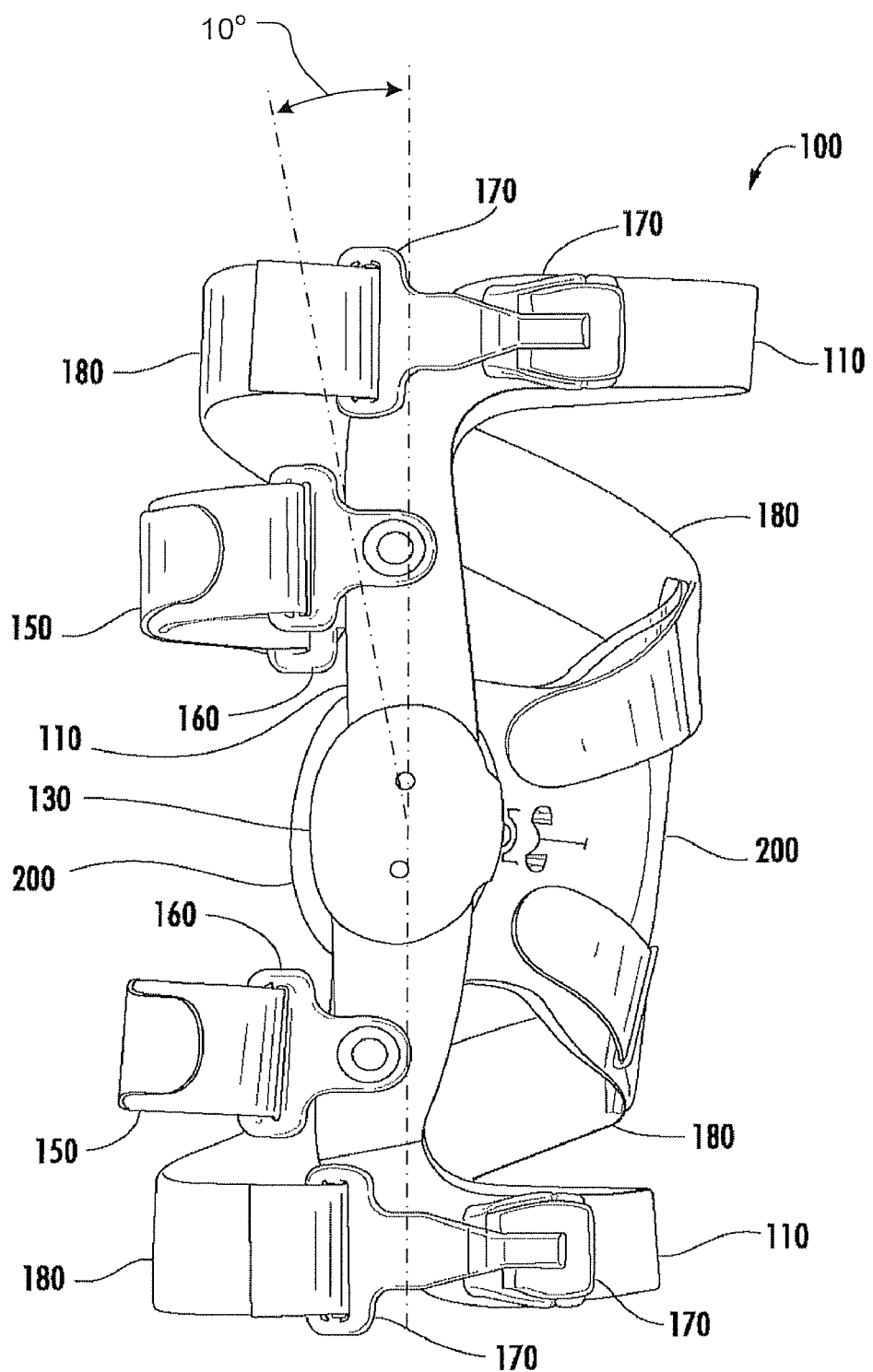
FIG. 1B is a front view of a patella brace according to a preferred embodiment of the present application.

Referring now to FIG. 1B, there is shown at 100 a front view of a patella brace according to a preferred embodiment of the present application. Straps 180 and straps 150 are oriented to fasten about a human appendage. Straps 150 are made of an inelastic material and are employed for securing the patella brace 100 to a human appendage. A strap 150 wraps from one side of rigid shell 110 to another side of rigid shell 110. Similarly another strap 150 wraps from one side of rigid shell 120 to another side of rigid shell 120. Straps 150 of rigid shells 110 and 120 act in concert to secure patella brace 110 to about a femur and a tibia. Straps 150 are made of hook and pile fasteners and are designed so that a portion of strap 150 may wrap against itself for self coupling. Straps 150 may optionally have pads coupled to them designed to aid grasping skin and in particular, skin having sweat buildup.

Figure 1C:
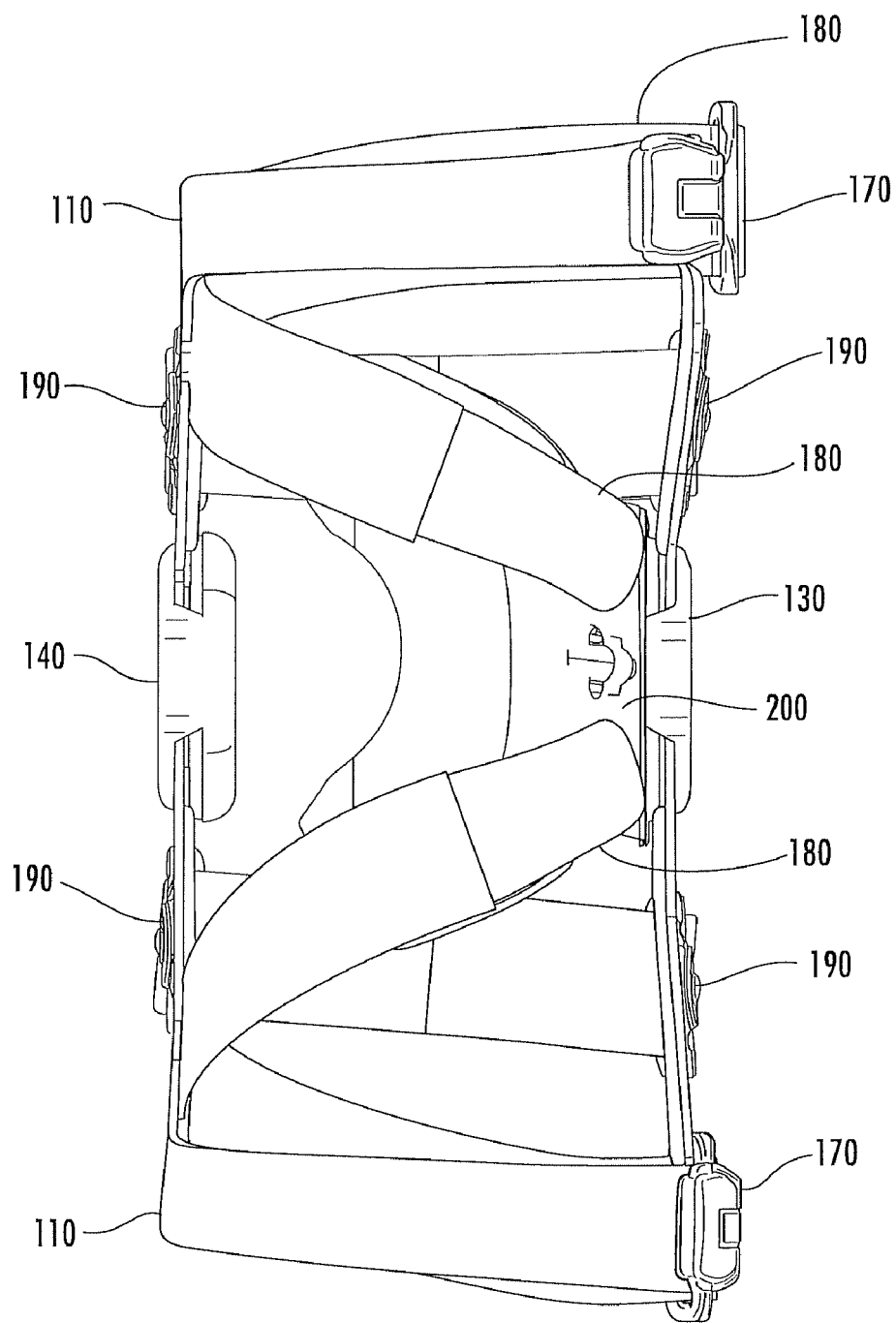
FIG. 1C is a left side view of a patella brace according to a preferred embodiment of the present application.

Referring now to FIG. 1C, there is shown at 100 a left side view of a patella brace according to a preferred embodiment of the present application. Straps 180 are made of hook and pile fasteners and are interspersed with elastic sections. A hook and pile component may be employed about one end of strap 180 for coupling to compression member 200 and interspersed by dual elastic bands coupling another section of hook and pile fasteners, which provides for self coupling about an opposing end of strap 180 via respective rigid shells 110 and 120. Straps 180 wrap from compression member 200 around a human appendage before self coupling to buckles 170. Buckles 170 are then fastened clamped in a resting position against rigid shells 110 and 120 to exert added tension in straps 180.

Strap restraints 160 are separated in a parallel manner about corresponding midpoints located on rigid shells 110 and rigid shell 120, to provide a maximum amount of coupling to a human appendage. Straps 150 are allowed to couple through strap restraints 160 to provide a maximum amount of leverage for fastening each of rigid shells 110 and 120 to a human appendage.

Figure 1D:
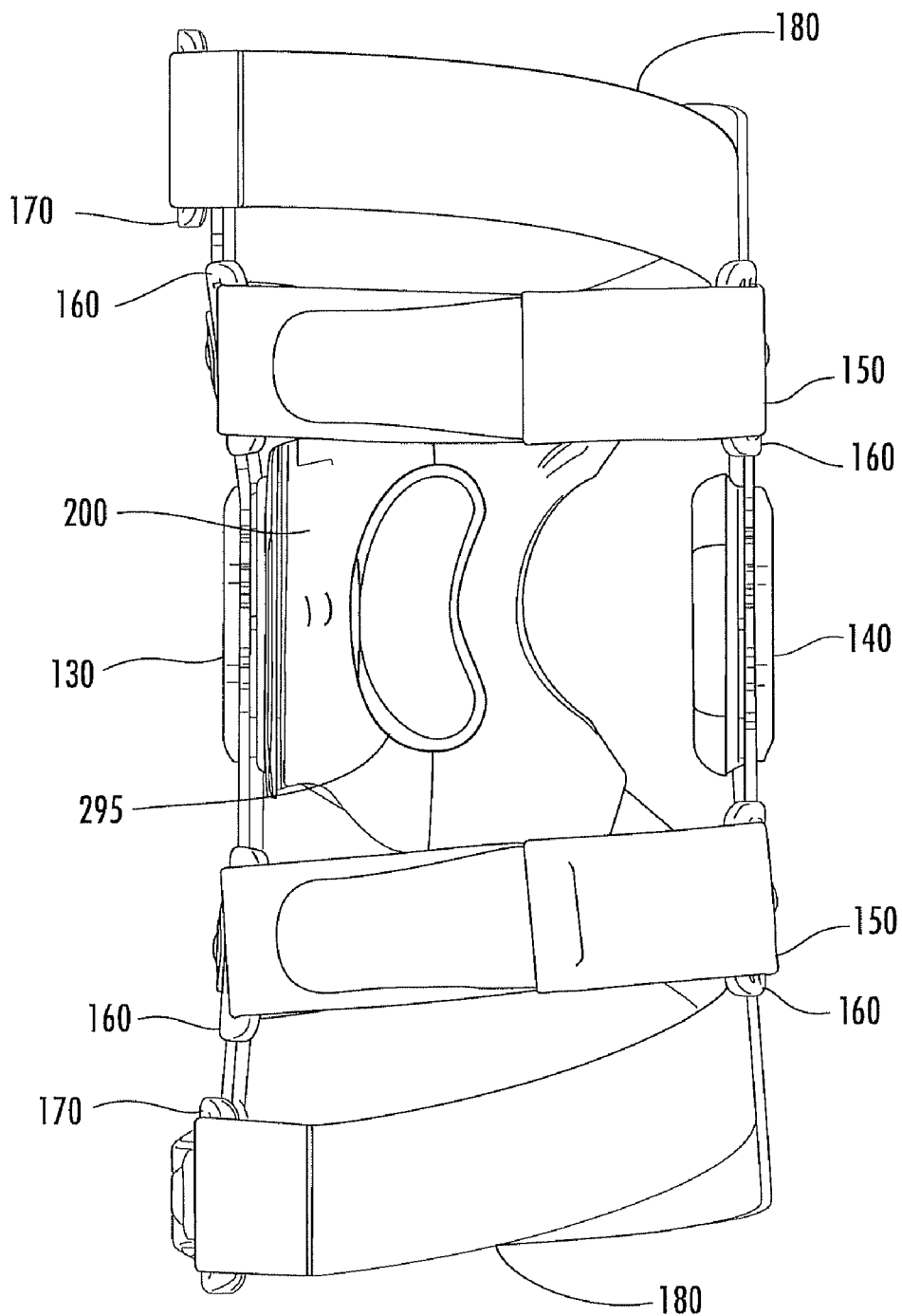
FIG. 1D is a right side view of a patella brace according to a preferred embodiment of the present application.

Referring now to FIG. 1D, there is shown at 100 a right side view of a patella brace according to a preferred embodiment of the present application. Buckles 170 are situated about the arcuate edges of rigid shells 110 and 120 for allowing a maximum amount of tension to be exerted about straps 180. Straps 180 are first abutted along a surface of rigid shells 110 and 120 before fastening in a tangential orientation along the surface of rigid shells 110 and 120 by having the buckles 170 located along the curvature of the rigid shells 110 and 120. Furthermore, buckles 170 supply indirect coupling means of straps 180 to rigid shells 110 and 120, allowing for maximum tension while providing a longer lifespan to straps 180.

Figure 1E:
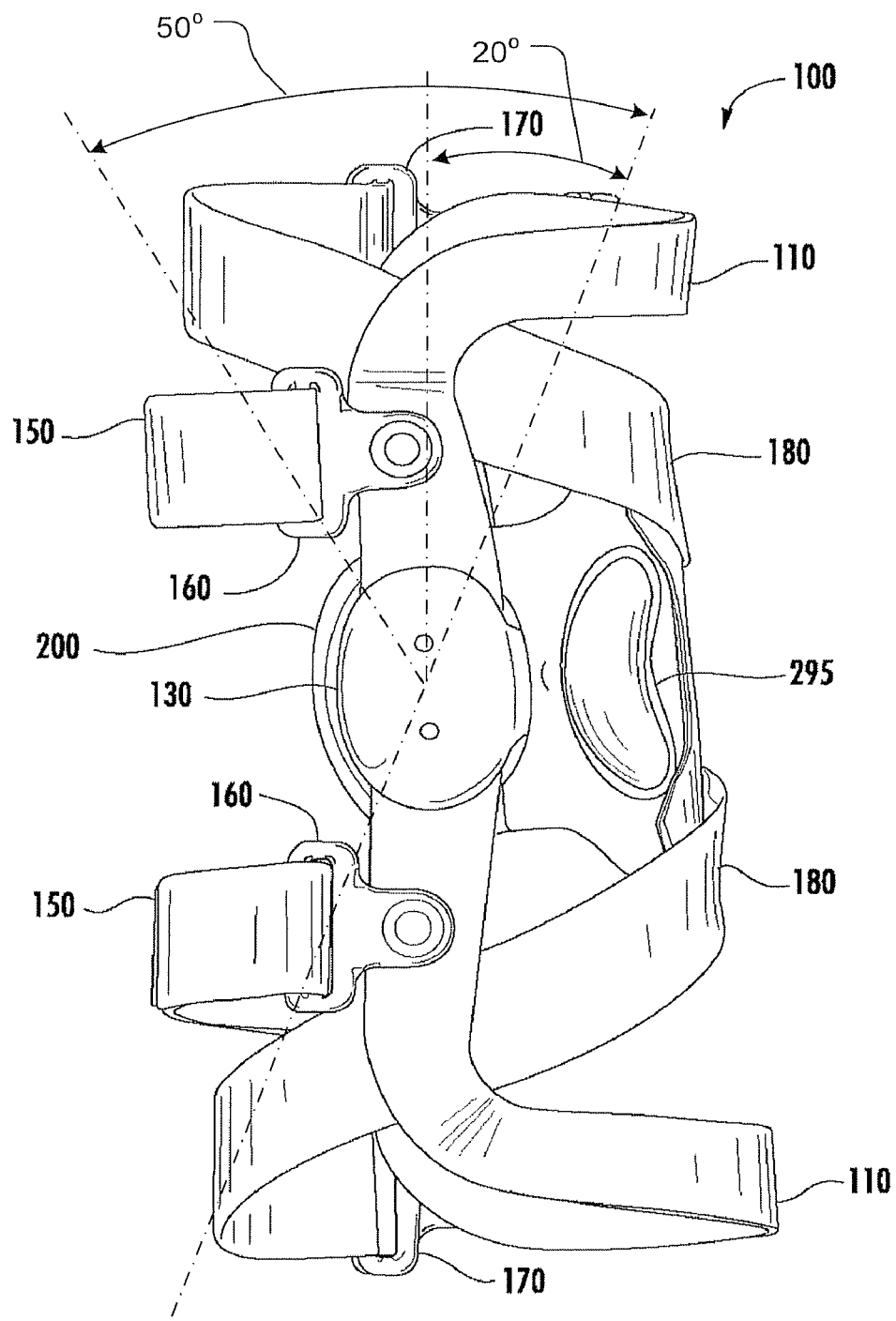
FIG. 1E is a back side view of a patella brace according to a preferred embodiment of the present application.

Referring now to FIG. 1E, there is shown at 100 a back side view of a patella brace according to a preferred embodiment of the present application. Hinge assemblies 130 and 140 are positioned relative to one another about the ends of rigid shells 110 and 120 to serve as pivot points in which rigid shells 110 and 120 may translate about one another. Hinge assemblies 130 and 140 are disposed about the edges of rigid shells 110 and 120 so that less force may be exerted about the arcuate curvature of rigid shells 110 and 120 to provide maximum translation of rigid shells 110 and 120 about hinge assemblies 130.

A user places his or her femur and tibia about the inner circumference rigid shells 110 and 120 of patella brace 100, with straps 150 and straps 180 loosened or released from strap restraints 160 and buckles 170. A strap 150 wraps about the femur and rigid shell 110 and threads through strap restraint 160. Another strap 150 wraps around the tibia and rigid shell 120 and threads through strap restraint 160. Each strap 150 pulls via strap restraint 160 to create tension and secures via a hook and pile structures incorporated on each respective strap 150. Strap 180 wraps from rigid shell 110, about a femur, and in between the inner circumference of rigid shell 110 and a wearer's leg and secures to hook and pile structures forming compression member 200. Another strap 180 wraps from rigid shell 120 around a tibia, between the inner circumference of rigid shell 120 and the tibia, and finally secures to hook and pile structures forming compression member 200.

Figure 2A:
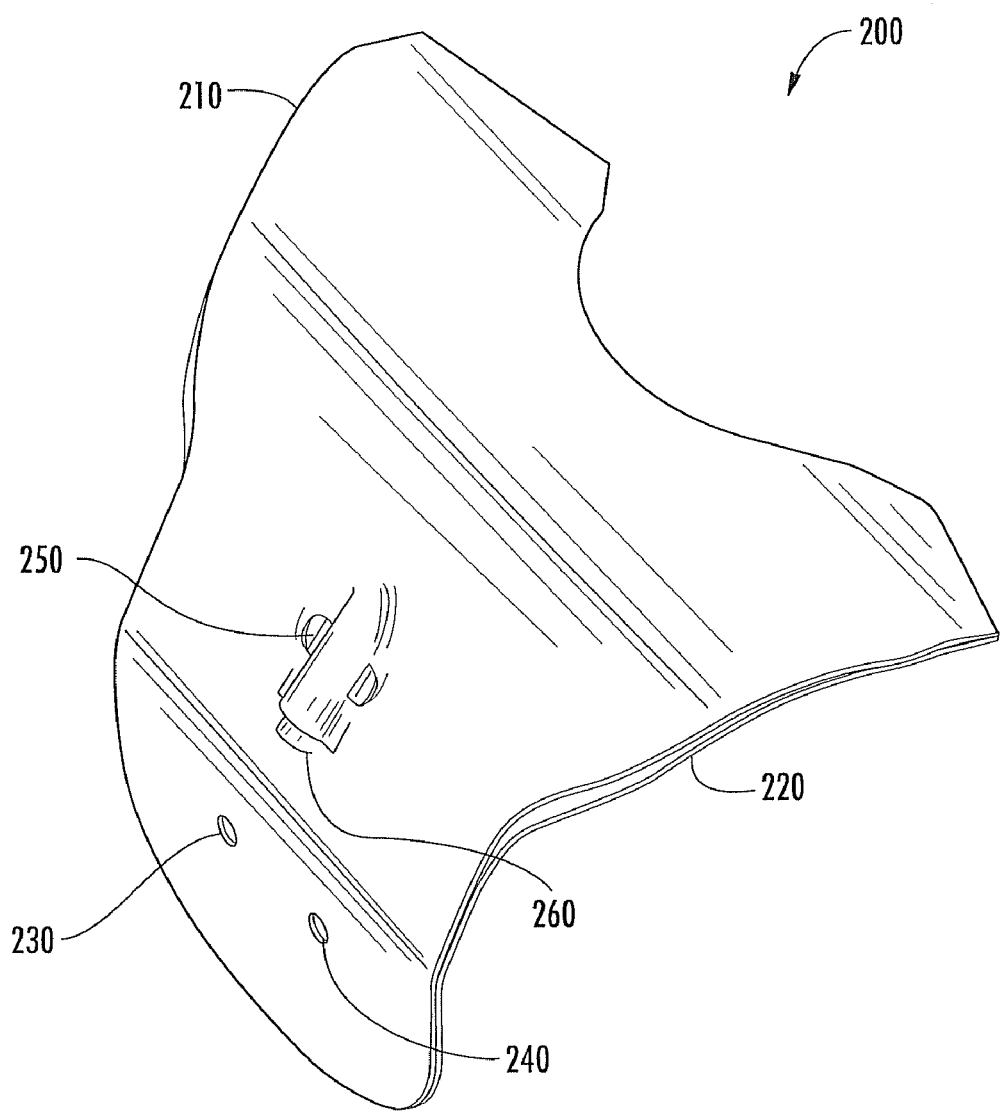
FIG. 2A is a perspective view of a compression member according to a preferred embodiment of the present application.

Pressure may be added to compression member 200, via a bladder 270 (as shown in FIG. 2A) after straps 180 secure to compression member 200. Additional support is provided to a wearer's patella by adding pressure to compression member 200.

In other embodiments, different mechanisms may be used to couple straps 180 to compression member 200. For example, zippers, buttons, snaps, or other types of fasteners may be employed to secure straps 180 to compression member 200. Additionally, in other embodiments, compression member 200 and straps 180 may be a singular component. For example, compression member 200 may be sewn, fastened, or coupled to straps 180 to form a singular component and attached to patella brace 100 about apertures 230 and 240 and buckles 170.

Referring now to FIG. 2A, there is shown at 200 a perspective view of a compression member according to a preferred embodiment of the present application. Compression member 200 is bending to illustrate the flexibility of compression member 200. A bladder nozzle 260 protrudes through an opening 250. The outer surface of compression member 200 is made of hook and pile pads 210 and 220. Hook and pile pads 210 and 220 may have straps coupled to them in order to create tension about compression member 200 for compressing a joint. Compression member 200 takes a generally Y-shaped form while having two spaced apertures 230 and 240 extending through hook and pile pads 210 and 220 for coupling the compression member 200 to hinge assembly 130. An opening 250 is illustrated to show that a nozzle 260 of a bladder 270 may protrude through hook and pile pad 210.

Figure 2B:
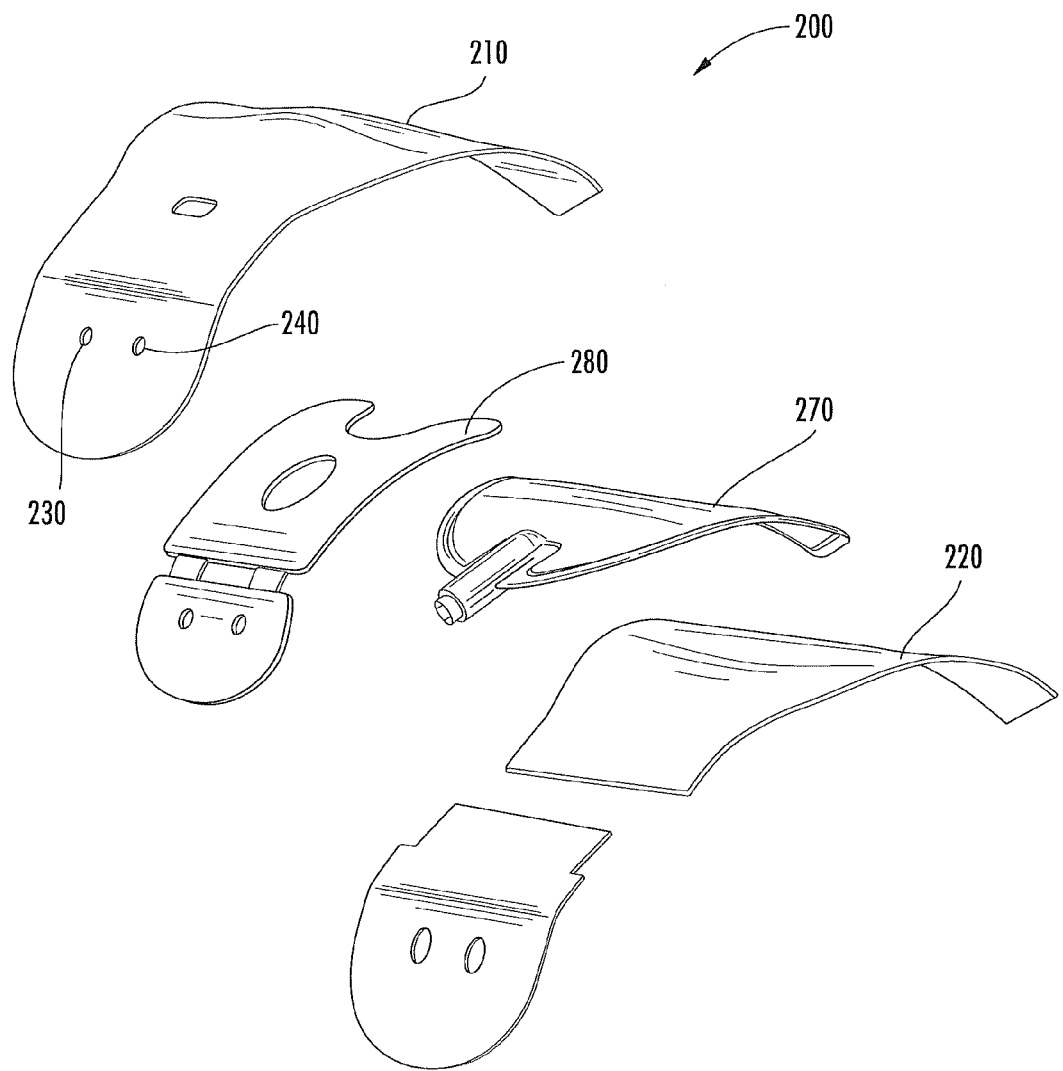
FIG. 2B an exploded view of a compression member according to a preferred embodiment of the present application.

Referring now to FIG. 2B, there is shown at 200 an exploded view of a compression member according to a preferred embodiment of the present application. As depicted, flexible plate 280 rests between hook and pile pad 210, bladder 270, and hook and pile pad 220. Flexible plate 280 lies generally adjacent to the curvature of hook and pile pad 210, and is capable of acting in concert with the various forces dispersed by bladder 270. Bladder 270 disperses the forces about flexible plate 280 as a user's patella begins to press against bladder 270. When pressure is exerted via straps 180, it is disseminated evenly via flexible plate 280 towards bladder 270 and absorbed by the user's patella, as necessary, due to tension exerted by straps 180 that restrain compression member 200. The amount and degree of such pressure may be adjusted according to the amount of pressure initially input into the bladder by the user.

Figure 2C:
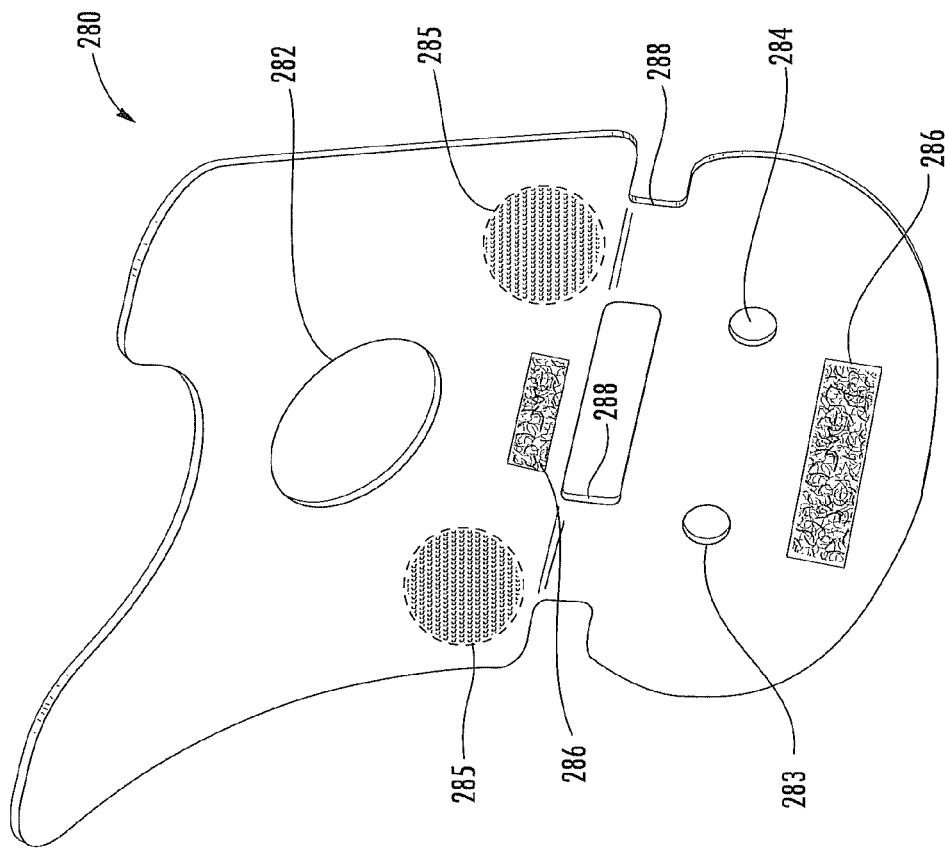
FIG. 2C is a frontal view of a flexible plate according to a preferred embodiment of the present application.

Referring now to FIG. 2C, there is shown at 280 a frontal view of a flexible plate according to a preferred embodiment of the present application. Flexible plate 280 has apertures 283 and 284 which correspond to apertures 230 and 240 of hook and pile pads 210 and 220. Additionally, flexible plate 280 has an opening 282, which corresponds to opening 250 of pile pad 210 for allowing protrusion of the nozzle 260 of bladder 270. Flexible plate 280 has generally curved edges which prevents flexible plate 280 protruding through hook and pile pads 210 and 220. Hook and pile inserts 285 and 286 provide for coupling of and restraint from sliding while flexible pad 280 is situated between hook and pile pads 210 and 220 and bladder 270. Flex control points 288 are oriented relative to apertures 283 and 284 for controlling the orientation and degree of bending of flexible plate 280.

Figure 2D:
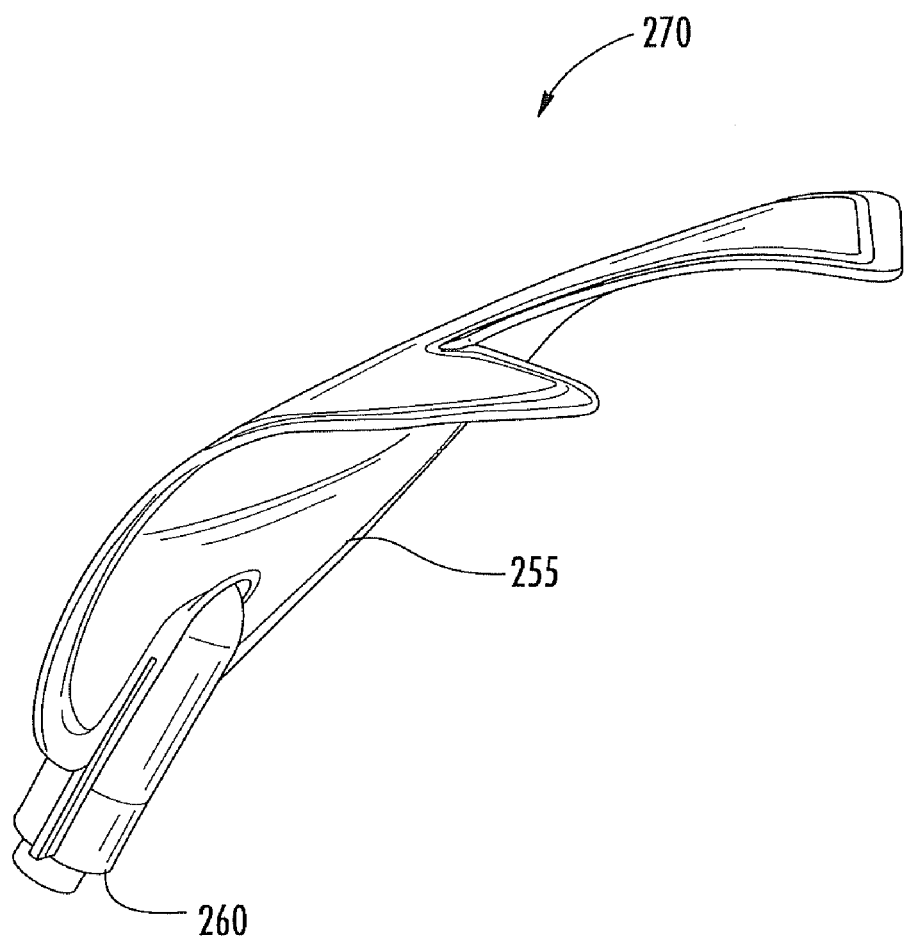
FIG. 2D is a perspective view of a bladder according to a preferred embodiment of the present application.

Referring now to FIG. 2D, there is shown at 270 a perspective view of a bladder according to a preferred embodiment of the present application. Bladder 270 has a nozzle 260 and a receptacle 255. Fluid, including but not limited to air, liquid, and gels may be input into bladder 270 via nozzle 260. Receptacle 255 is formed in a generally Y-shaped fashion to conform about the shape of hook and pile pads 210 and 220. Nozzle 260 is designed so that additional fluid may not enter bladder 270 when receptacle 255 is filled to capacity. Similarly, nozzle 260 is designed to prevent implosion of receptacle 255 when receptacle is diminished of its capacity.

Figure 2E:
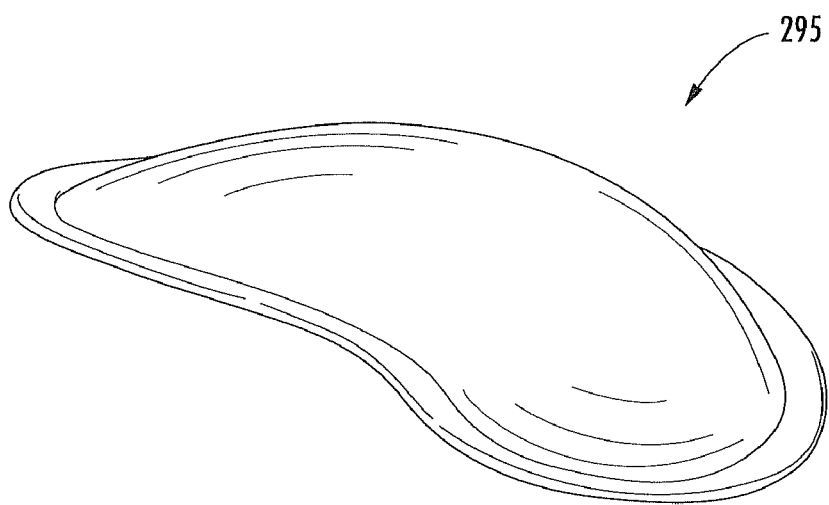
FIG. 2E is a perspective view of a cushion according to a preferred embodiment of the present application.

Referring now to FIG. 2E, there is shown at 295 a perspective view of a cushion according to a preferred embodiment of the present application. Cushion 295 may be optionally coupled to hook and pile pads 210 and 220 of compression member 200. Cushion 295 is shaped in a rounded fashion to conform to a patella. Though not depicted, cushion 295 has a substantially flat side adapted to be removably coupled to a hook and pile adaptation of compression member 200. Cushion 295 is capable of being removably coupled to various points of compression member 200. Cushion 295 may be fashioned to align with a wearer's patella in order to prevent a patella from slipping out of the medial groove.

In operation, bladder 270 and flexible plate 280 may be inserted between hook and pile pads 210 and 220 of compression member 200. Flexible plate 280 may be inserted between and secured to hook and pile pads 210 and 220 via hook and pile inserts 285 and 286, after inserting bladder 270 between hook and pile pads 210 and 220 of compression member 200. Nozzle 260 of bladder 270 can be inserted through opening 282 of flexible plate 280 and opening 250 of compression member 200. Bladder 270 is oriented so that is may be located between a wearer's patella and flexible plate 280. Pressure may be added or decreased from bladder 270 as desired. Flexible plate 280 is made of a material that provides for flexibility, but greater flex is provided by flex control points 288, when flexible plate 280 is secured to hinge assemblies 130 and 140 via apertures 283 and 284. Flexible plate 280 is made of a rigid, yet elastic material in order to supply an opposing force exerted by bladder 270. The greater the amount of pressure input into bladder 270, the greater the corresponding force against bladder 270 exerted by flexible plate 280. The less the amount of pressure removed from bladder 270, the lower the corresponding force exerted by flexible plate 280.

Pressure may be added or decreased from compression member 200 as desired to allow for greater or less restraint of a patella once a user has coupled the knee brace 100 to his or her tibia and femur, and straps 150 and straps 180 have been secured. A pump device (not shown) may be temporarily coupled to the nozzle 260 of bladder 270 to increase or decrease pressure within compression member 200. Straps 180 draw in tension when pressure is increased and in turn increase the strength of the hook and pile connections between compression member 200 and straps 180. Straps 180 release tension as pressure is decreased and in turn reduce the strength of the hook and pile connections between compression member 200 and straps 180.

In an alternate embodiment, compression member 200 may take other shapes and be made of other materials, so long as allowing for coupling of a member. For example, compression member 200 may be generally X-shaped, generally rectangular, generally ovular, or generally circular.

In other embodiments of the present application, flexible plate 280 may take other shapes, so long as it conforms to the bounds of hook and pile pads 210 and 220. For example flexible plate 280 may be formed in a generally X-shaped fashion if hook and pile pads are shaped in a generally X-shaped fashion. Opening 282 may take a form other than being substantially circular and may also vary in size. For example, opening 282 may be sized to snugly fit around a nozzle 260. Also, opening 282 may be generally rectangular to create restrained yet slight degree of movement of nozzle 260.

Alternatively, a single aperture similar to 283 and 284 may be used to couple flexible plate 280 to hinge assembly 130. Alternatively, in yet other embodiments of the present application, a multitude of apertures similar to 283 and 284 may be used to couple flexible plate 280 to a hinge assembly 130. Also, in other embodiments, a single flex control point similar to flex control points 288 may be employed. Alternatively, in yet other embodiments of the present application, any number of flex control points may be used to provide additional flexibility of patella plate 280.

Furthermore, bladder 270 may take other forms. For example, if compression member 200 is shaped in a generally X-shaped fashion, bladder 270 may be shaped in a generally X-shaped fashion. Additionally, bladder 270 need not necessarily be fashioned to have a single chamber capable of receiving a fluid. In other embodiments, bladder 270 may have several chambers which may contain fluids. Similarly, multiple nozzles may be employed for inserting or removing fluid from bladder 270. At the same time, multiple bladders may faceted about compression member 200 for receiving fluid. It should also be noted that bladder 270, may receive several types of fluid. For example, in the event that bladder 270 is fashioned to have multiple chambers, one chamber may contain a gel, while the other may be fashioned for receiving air or another fluid. Multiple bladders may contain multiple fluids and may be operatively associated with one another.

Moreover, cushion 295 may be shaped in any form or fashion and any number of cushions 295 may be employed. For example, in alternative embodiments of the present application, a single circular cushion may be employed to fully surround and embrace a wearer's patella. In other embodiments, a single half circular cushion may be employed to embrace a wearer's patella. It should also be understood that in other embodiments, other fastening devices such as snaps, buttons, and zippers may be employed for coupling cushion 295 to compression member 200.

Figure 3A:
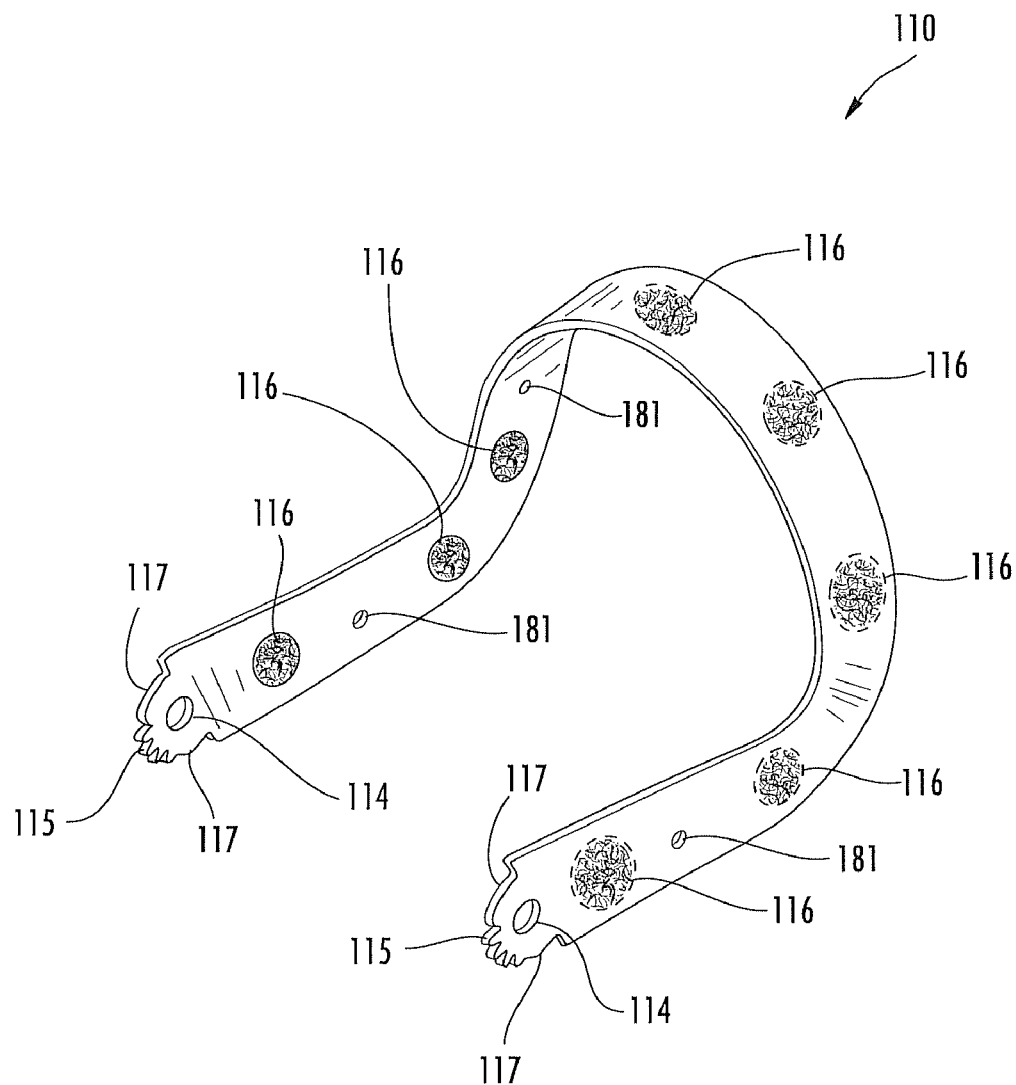
FIG. 3A is a perspective view of a first rigid shell according to the present application.
Figure 5A:
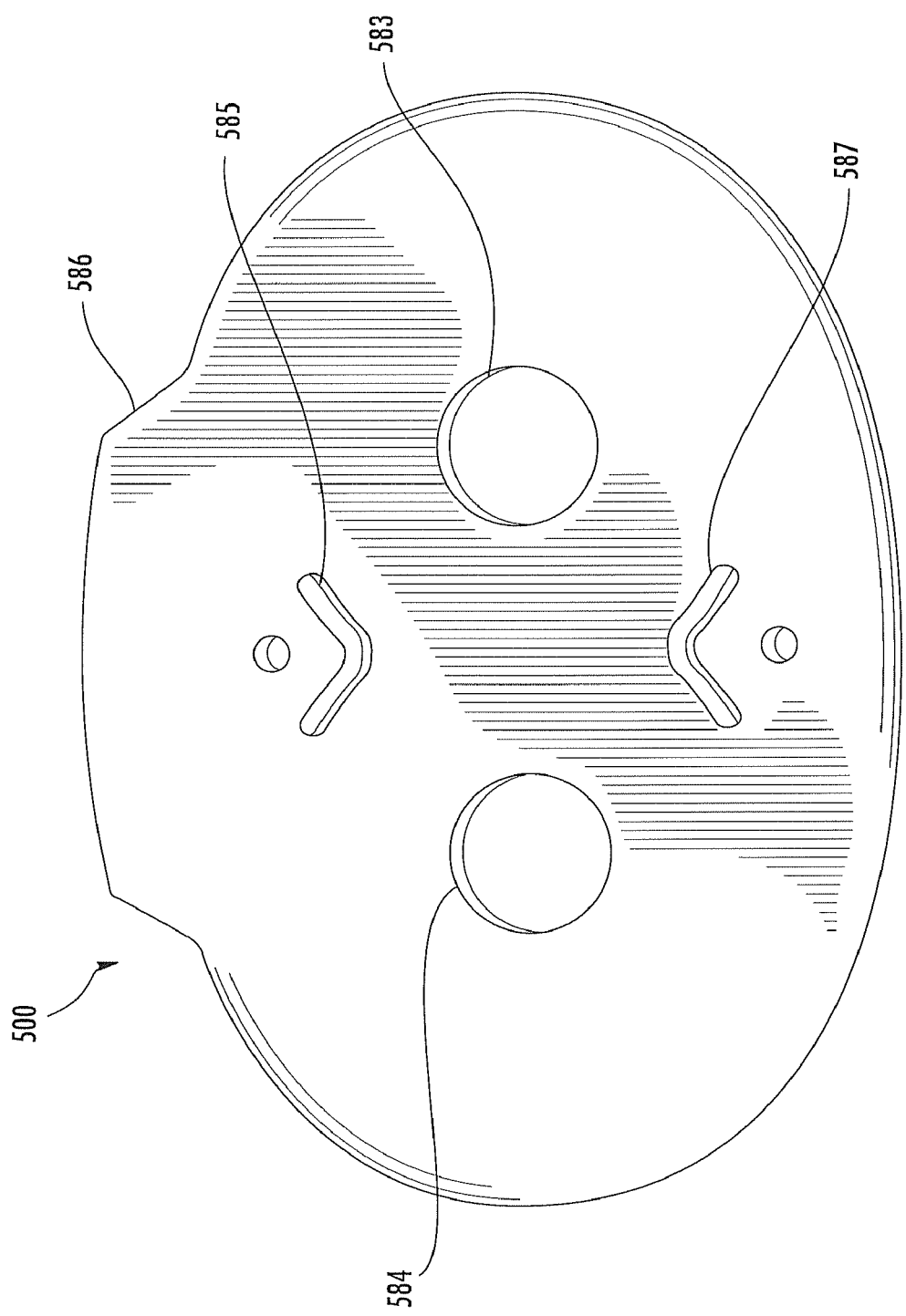
FIG. 5A is a rear view of a logo plate according to the present application.

Referring now to FIG. 3A, there is shown at 110 a perspective view of a first rigid shell of the patella brace according to the present application. Rigid shells 110 and 120 have apertures 181 for allowing fasteners (as shown in FIG. 1) to couple various components such as buckles (as shown in FIG. 1). Additionally, hook and pile padding adaptations 116 are coupled about the perimeter of rigid shells 110 and 120 to allow for coupling of padding. Mate points 115 form about the ends of rigid shell 110. Mate points 125 form about the ends of rigid shell 120. Pivot apertures 114 are formed central to mate points 115. Pivot apertures 123 are formed central to mate points 125. Mate points 115 and mate points 125 are formed to mate with one another to allow translation of rigid shells 110 and 120 about common axes. Limiting curves 117 are formed about the edge of mate points 115. Limiting curves 127 are formed about the edge of mate points 125. Limiting curves 117 and 127 are formed cooperate with a motion limiter 585 (as shown in FIG. 5A). In a preferred embodiment of the present invention, mate points 115 and 125 are gears.

Figure 3B:
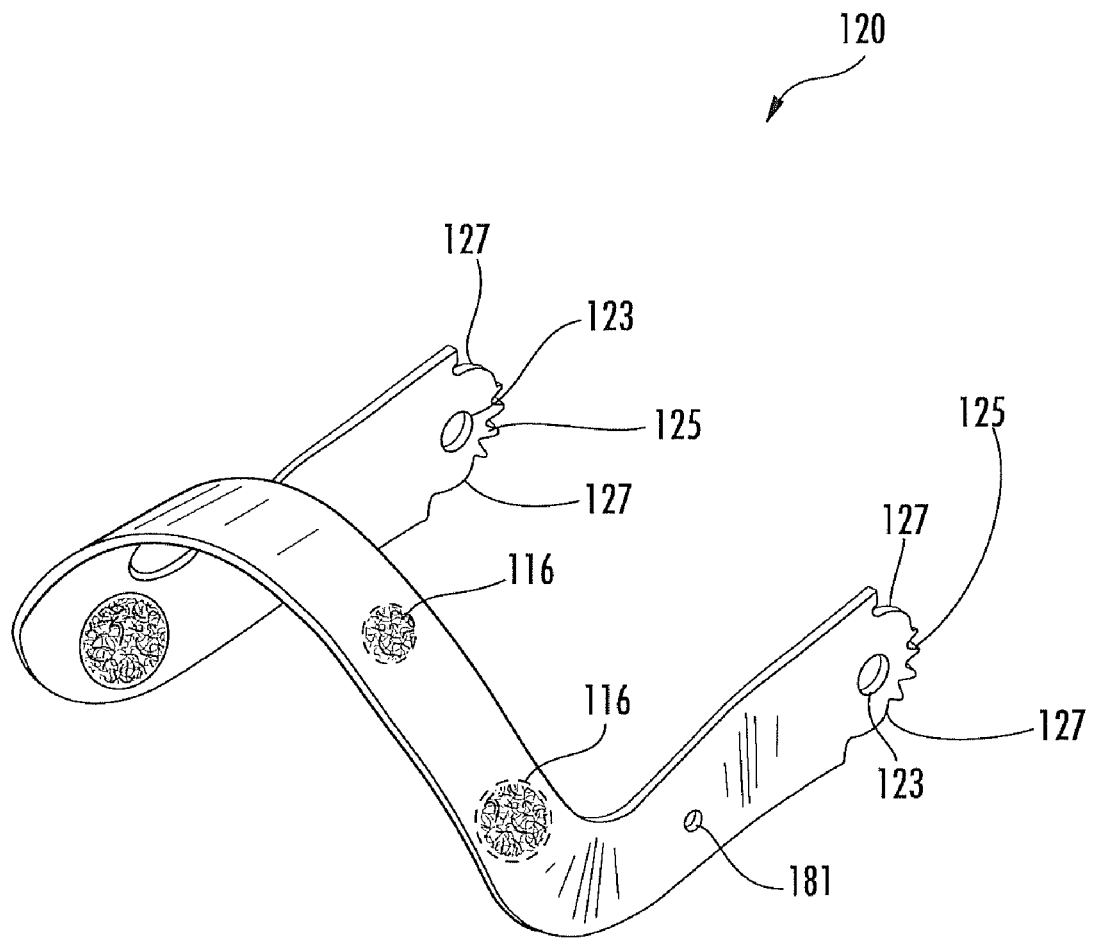
FIG. 3B is a perspective view of a second rigid shell according to the present application.

Referring now to FIG. 3B, there is shown at 120 a perspective view of a second rigid shell of the patella brace according to the present application. Mate points 115 and mate points 125 are oriented to allow for transition of rigid shells 110 and 120 about a central axis that runs about pivot apertures 114 and pivot apertures 123. Rotation occurs via mate points 115 and 125 about pivot apertures 114 and pivot apertures 123 as motion is exerted about rigid shells 110 and 120. Rigid shells 110 and 120 are prevented from further rotation via limiting curves 117 and 127 when rigid shells 110 and 120 translate to the extent allowed by mate points 115 and 125.

Figure 4:
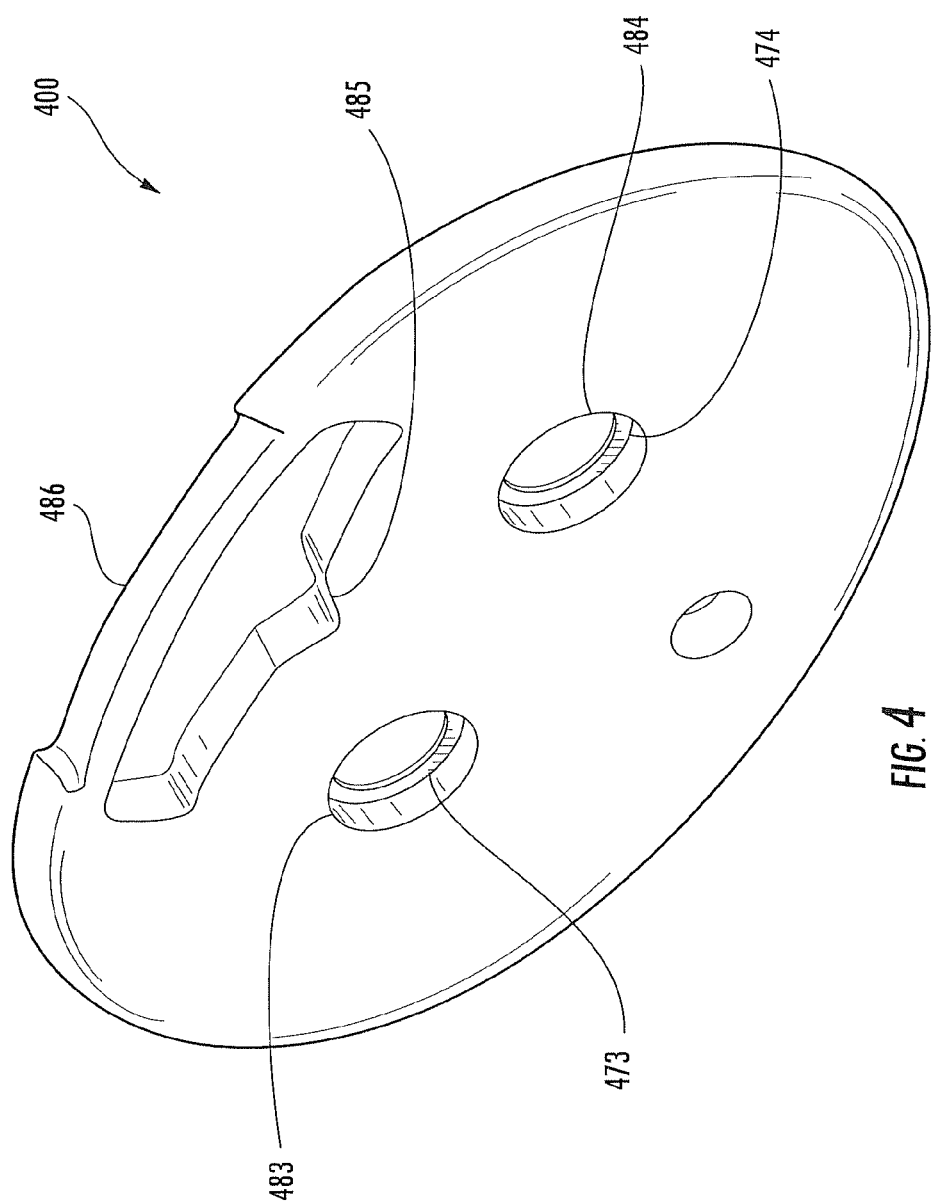
FIG. 4 is a perspective view of a hinge plate according to the present application.

Referring now to FIG. 4, there is shown at 400 a perspective of a hinge plate of the patella brace according to the present application. Hinge plate 400 takes a generally ovular shape and has several apertures. Apertures 483 and 484 protrude through hinge plate 400 and are employed to couple hinge plate 400 to rigid shells 110 and 120, and logo plate 500. Abutting edges 473 and 474 extending within apertures 483 and 484. Abutting edges 473 and 474 provide securing means for coupling members 443 and 444 to grasp to hinge plate 400 for coupling to logo plate 500 (as shown in FIG. 5C). Apertures 483 and 484 correspond to align with apertures 283 and 284 for optionally coupling compression member 200 via apertures 230 and 240 to hinge plate. A groove 485 corresponds with a motion restraint 585 of logo plate 500 to restrain movement of rigid shells 110 and 120. Furthermore, a lip receiving stabilizer 486 is oriented to couple with a lip adaptation 586 of logo plate 500 to keep logo plates 400 and 500 aligned. Optionally disposed about a surface of hinge plate 400 are hook and pile fasteners to provide comfort and optionally allow coupling of padding.

Referring now to FIG. 5A, there is shown at 500 a rear view of a logo plate according to the present application. Logo plate 500 has apertures 583 and 584 for coupling hinge plate 400 through corresponding apertures 483 and 484. Logo plate 500 aligns about apertures 583 and 584, apertures 483 and 484 of hinge plate 400, and pivot apertures 114 and pivot apertures 123 of rigid shells 110 and 120, respectively, for coupling. Motion limiters 585 and 587 prevent rigid shells 110 and 120 from over extending by protruding from logo plate 500.

Figure 5B:
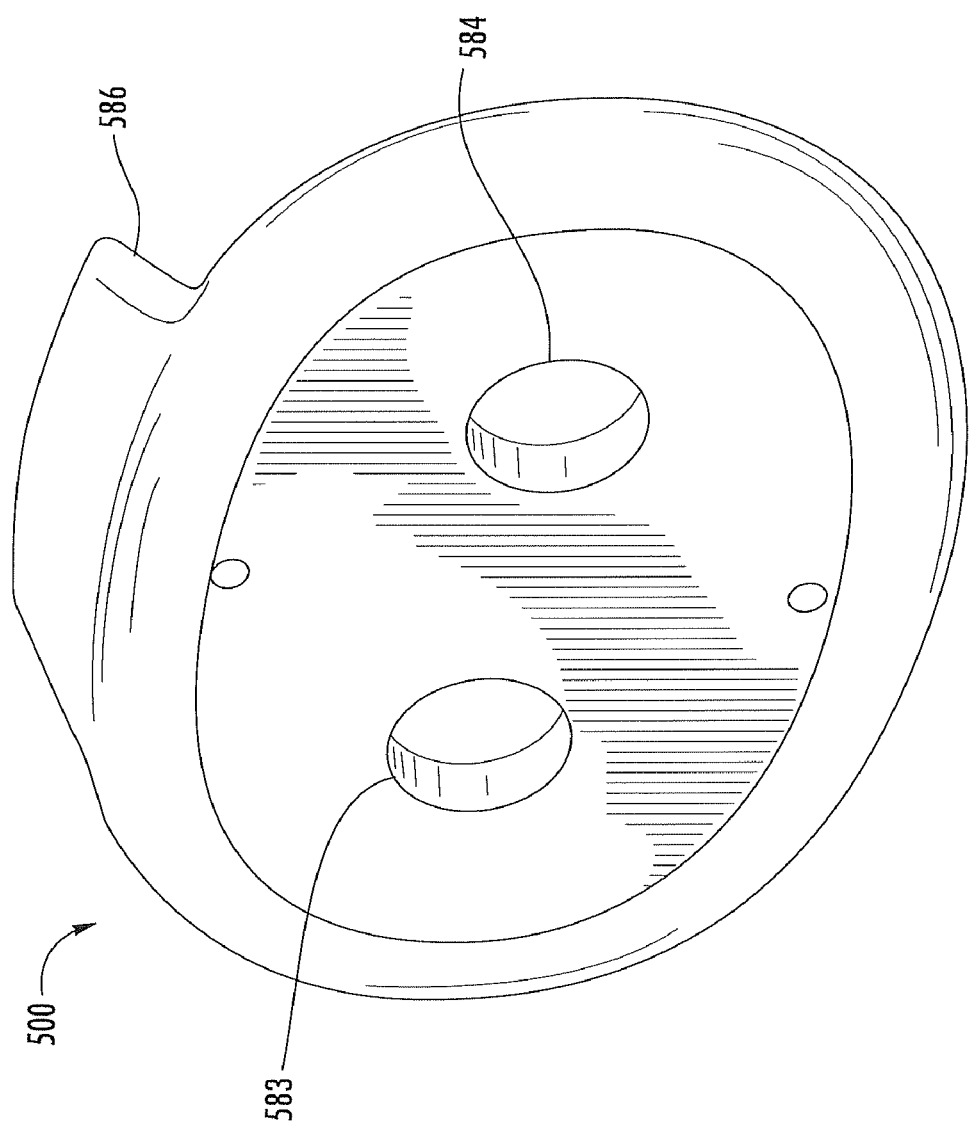
FIG. 5B is a perspective view of a logo plate according to the present application.
Figure 5C:
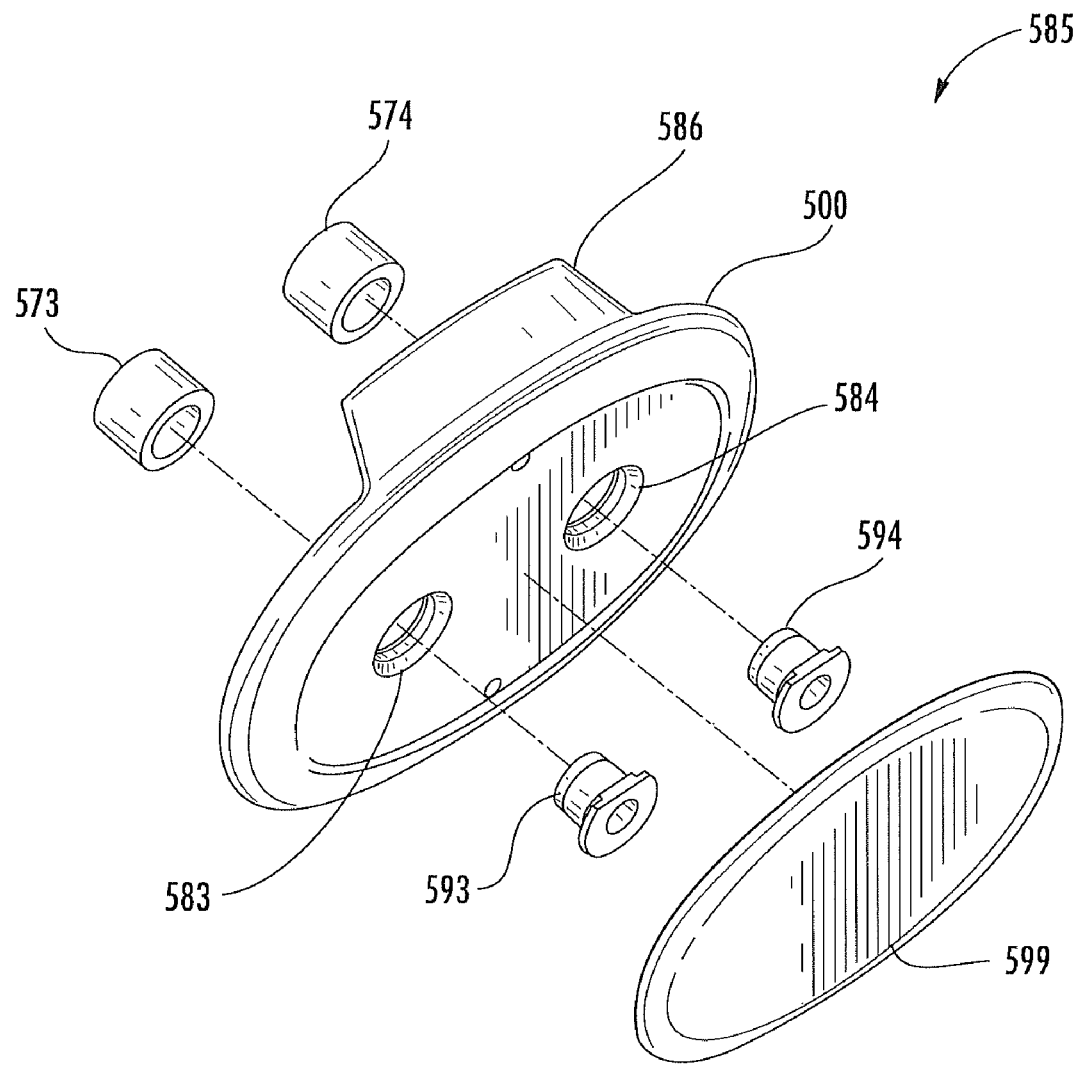
FIG. 5C is an exploded view of a logo plate and attaching components of the patella brace according to the present application.

Referring now to FIG. 5B, there is shown at 500 a perspective view of a logo plate according to the present application. Lip adaptation 586 protrudes from the circumference of logo plate 500 to further stabilize the orientation of logo plate 500 and hinge plate 400. Lip adaptation 586 tapers as it extends from the circumference of logo plate 500 in order to mate with lip receiving stabilizer 486. As rigid shells 110 and 120 translate about hinge plates 400 and logo plates 500, their range of motion is restrained upon contacting motion limiters 585 and 587. Hook and pile fasteners may be optionally disposed about a surface of logo plate 500 to provide for coupling of padding.

In alternate embodiments of the present application, several components may be included. For example, two lip adaptations may be aligned to mate with several lip receiving stabilizers about the circumference of a hinge plate. Additionally, in other embodiments, a lip adaptation 586 may extend from the logo plate about an interior surface location. Furthermore, motion limiters 586 and 587 may slope at a different angle, to provide more or less constraint for translation of rigid shells 110 and 120 (as shown in FIGS. 3A and 3B). Additionally, apertures 583 and 584 may be located closer to, or further from, one another to define more precise or less precise ranges of motion to rigid shells 110 and 120 (as shown in FIGS. 3A and 3B).

Referring now to FIG. 5C, there is shown at 585 an exploded view of a logo plate with attaching components of the patella brace according to the present application. Hinge screw receiving means 593 and 594 along with bushings 573 and 574 are aligned about apertures 583 and 584 of logo plate 500. Lip adaptation 586 protrudes about a rear edge of logo plate 500. Logo cover 599 aligns to cover a portion of logo plate 500.

Lip adaptation 586 is formed to join with lip receiving stabilizer 486 for further stabilizing the union of hinge plate 400 and logo plate 500. Bushings 573 and 574 are situated between logo plate 500 and hinge plate 400, while aligned with apertures 483 and 484 of hinge plate 400, and apertures 583 and 584 of hinge plate 500. Bushings 573 and 574 fit within pivot apertures 114 and pivot apertures 123 of rigid shells 110 and 120 to keep hinge plate 400 and logo plate 500 spaced apart while allowing rigid shells 110 and 120 to translate relative to one another in a defined range of motion. Bushings 573 and 574 are restrained by abutting edges 473 and 474 of hinge plate 400 and screw receiving means 593 and 594. Sets of coupling members 443 and 444 couple rigid shells 110 and 120 between hinge plate 400 and logo plate 500 by fastening to screw receiving means 593 and 594. Logo cover 599 is faceted atop a portion of logo plate 500. Logo cover 599 acts to cover screw receiving means 593 and 594 of logo plate 500 and to optionally display a logo.

Figure 6:
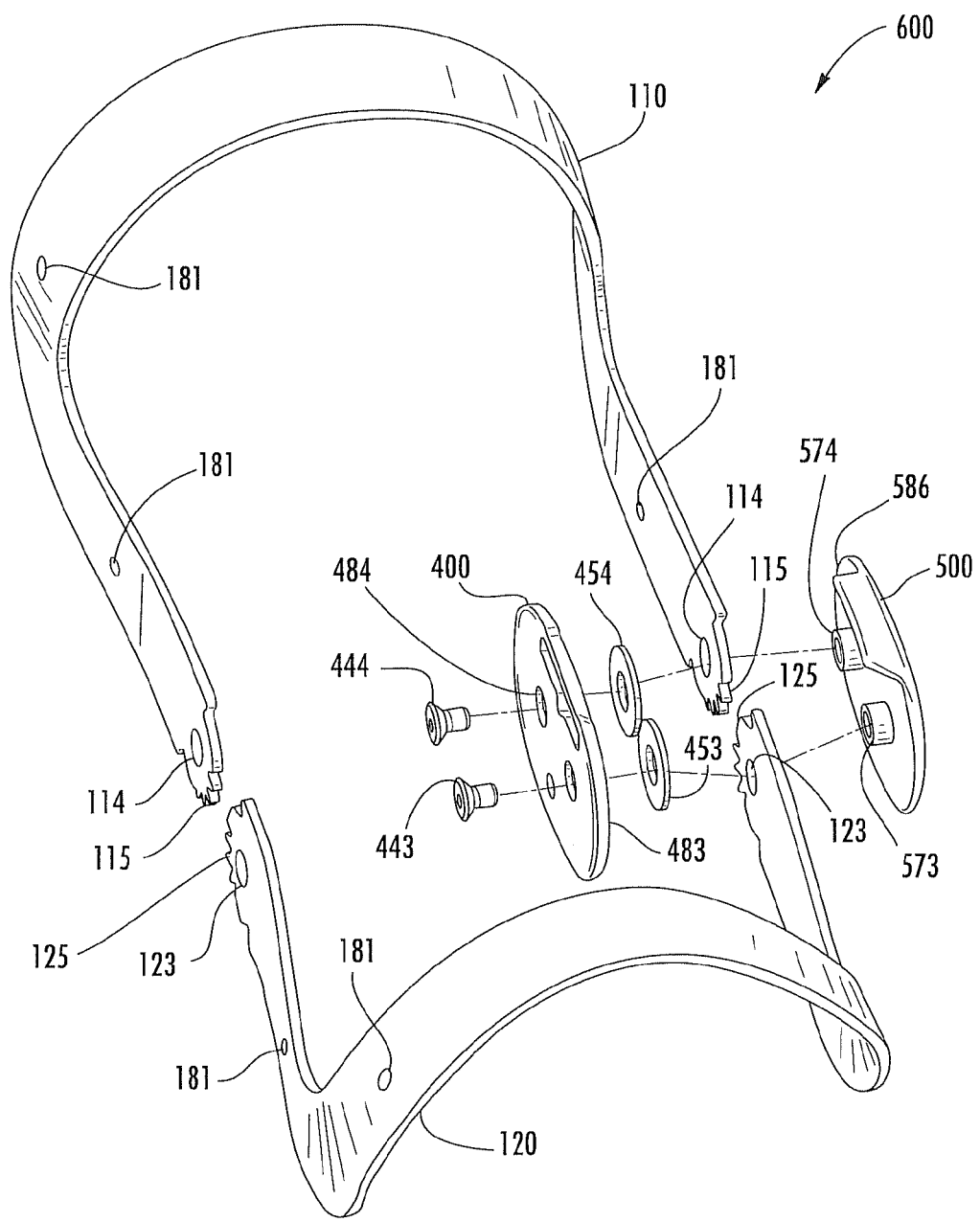
FIG. 6 is an exploded view of the patella brace separated from a hinge assembly according the present application.

Referring now to FIG. 6, there is shown at 600 an exploded view of the patella brace separated from a first hinge assembly according the present application. Mate points 115 and 125 along with pivot apertures 114 and pivot apertures 123 are aligned about central axes that allow coupling to, and translation about, hinge plate 400 and logo plate 500 of rigid shells 110 and 120. Bushings 574 and 573 of logo plate 500 couple to pivot apertures 114 and 123 of rigid shells 110 and 120 respectively. Washers 454 and 453 couple about hinge plate 400 and pivot apertures 114 and 123 of rigid shells 110 and 120. Coupling members 444 and 443 act to couple hinge plate 400 via apertures 484 and 483, pivot points, 114 and pivot points 123 along with bushings 574 and 573 to logo plate 500 and rigid shells 110 and 120. Lip adaptation 586 further secures hinge plate 400 about lip receiving stabilizer 486 to logo plate 500. Apertures 181 allow for components to be fastened to rigid shells 110 and 120. Hinge plates 400 and logo plates 500 correspond to provide coaxial translation of rigid shells 110 and 120.

Figure 7:
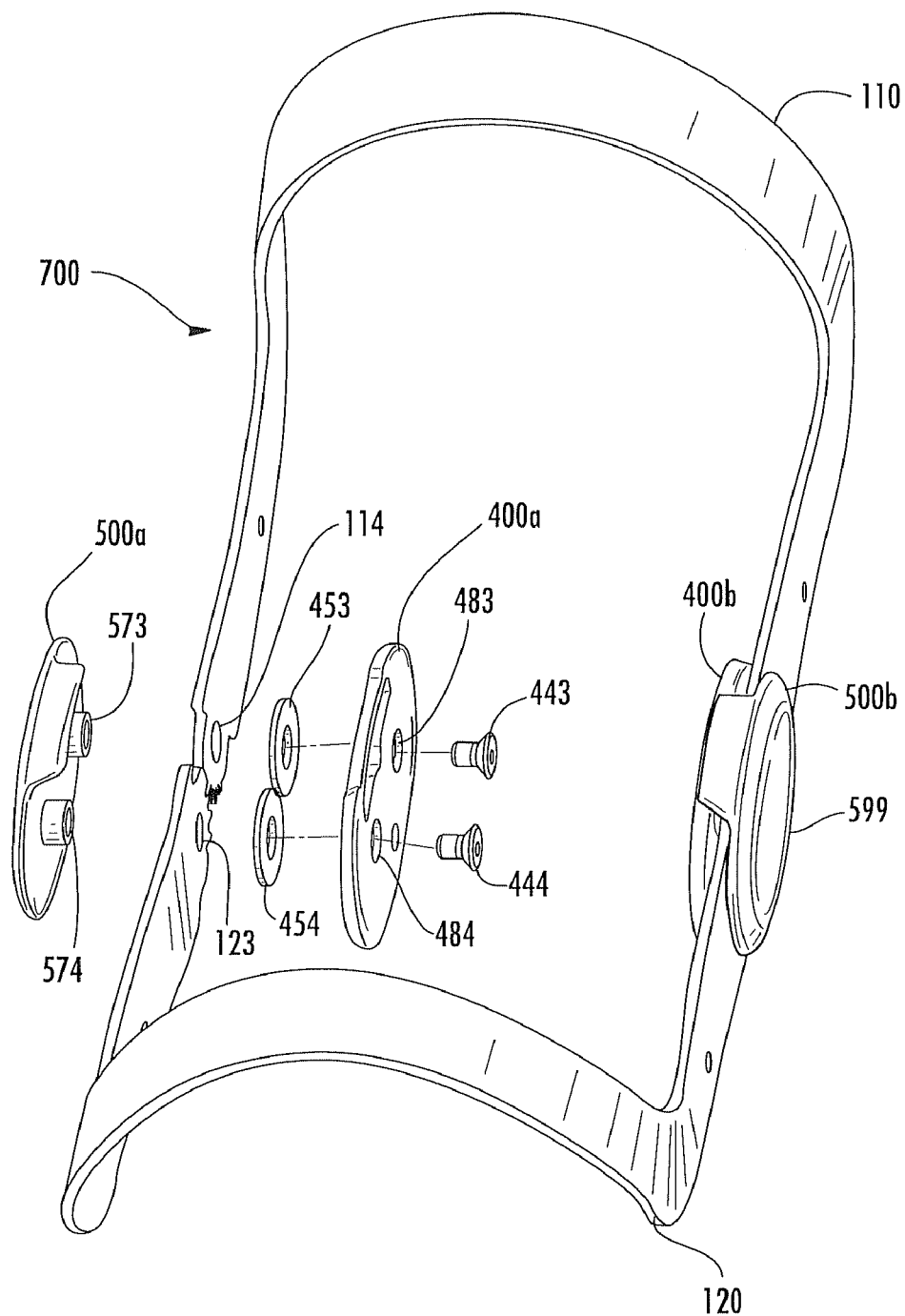
FIG. 7 is an exploded view of the patella brace coupled about a hinge assembly and separated from another hinge assembly according to the present application.

Referring now to FIG. 7, there is shown at 700 an exploded view of the patella brace coupled by a first hinge assembly and separated from a second hinge assembly according to the present application. Accordingly, an isometric view of hinge plates 400a and 400b and logo plates 500a and 500b mating about rigid shells 110 and 120 is shown. Rigid shell 110 is aligned about and mated with rigid shell 120. Hinge plate 400b couples to logo plate 500b. Logo plate 500b is covered by a logo cover 599. Coupling members 444 and 443 are aligned to couple hinge plate 400a and logo plate 500a to rigid shells 110 and 220 via apertures 484 and 483, washers 454 and 453, pivot points 123 and 114, and bushings 574 and 573 respectively. Hinge plate 400a is adapted to be coupled to a logo plate 500b to allow for coaxial translation of rigid shells 110 and 120. Rigid shells 110 and 120 can coaxially translate about central axes through coupling to hinge plates 400a and 400b to logo plates 500a and 500b.

Figure 8:
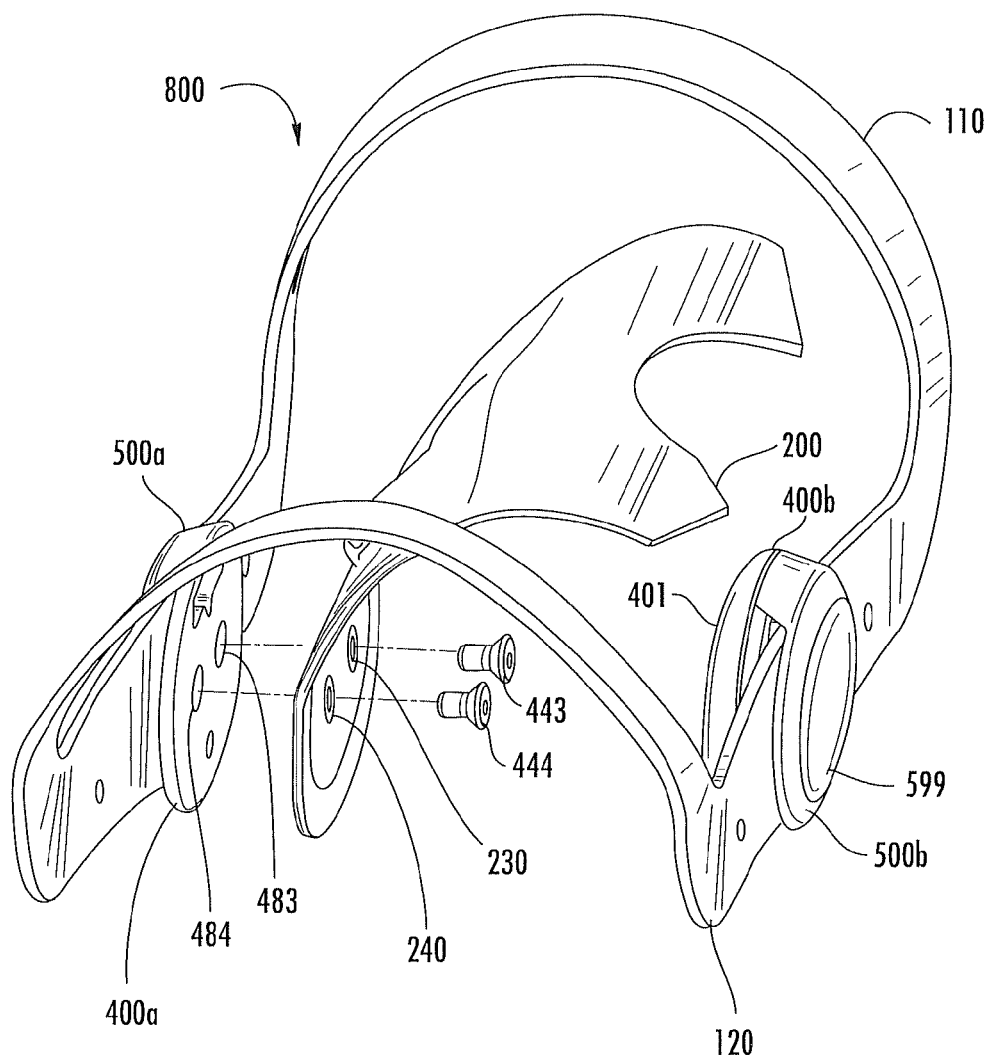
FIG. 8 is an exploded view of the patella brace with rigid shell assembly separated from a compression member according to the present application.

Referring now to FIG. 8, there is shown at 800 an exploded view of the patella brace with rigid shell assembly separated from a compression member according to the present application. Patella brace 100 has a compression member 200, coupled about rigid shells 110 and 120. As is depicted, a compression member 200 is aligned about apertures 484 and 483 of hinge plate 400a. Coupling members 444 and 443 are aligned about apertures 240 and 230 of compression member 200 and apertures 484 and 483 of hinge plate 400a. Coupling members 444 and 443 operatively couple compression member 200 to hinge plate 400b. Side pad 401 is coupled to hinge plate 400b via a hook and pile structure. Side pad 401 provides cushioning to a wearer's knee to prevent direct contact by a hinge plate, or other component of a patella brace 100, against a wearer's knee. Also depicted, is logo cover 599 coupled to logo plate 500. In an alternate embodiment of the present application, compression member 200 may be optionally coupled to hinge plate 400b and hook and pile structure 401 may be optionally coupled to hinge plate 400a.

The patella brace 100 is prohibited from "rolling" from a wearer's patella via the composure and shape of rigid shells 110 and 120 coupling to a wearer's femur and tibia respectively. The interaction between rigid shells 110 and 120, hinge plates 400a and 400b, and logo plates 500a and 500b restrains and controls the motion allowed by patella brace 100. As rigid shells 110 and 120 laterally interact with one another, hinge plates 400a and 400b remain aligned with one another and central to a wearer's patella, to control the ability of and degree of lateral motion of rigid shells 110 and 120.

Compression member 200 couples directly to hinge plate 400a and logo plate 500a as well as the wearer's femur and tibia via straps, the allowable degree of motion and movement depends on movement of the wearer's leg. As a wearer's bends his or her leg, the straps attaching compression member 200 to the femur and tibia of a wearer's leg, cause a corresponding motion of compression member 200. Hence, the greater the degree of bend in a wearer's leg, the greater the restraint provided on a wearer's patella by compression member 200.

Patella brace 100 supplies a causal relationship between the interaction of rigid shells 110 and 120 and compression member 200. A wearer's patella is subjected to direct compression, rather than torsion due to the straps connection between compression member 200, around a wearer's femur and tibia, and coupling to rigid shells 110 and 120, respectively. Straps 180 cause compression member 200 to exert compression in a direction generally normal to a wearer's patella as a wearer bends his or her femur and tibia, and rigid shells 110 and 120 transition accordingly. Compression member 200 exerts direct compression on a patella, rather than supplying offsetting torsional forces when a wearer's femur and tibia bend between 20 and 50 degrees. A patella is able to remain aligned about the medial groove by having forces applied directly normal to a wearer's patella to allow for lateral motion while deterring subluxation. Since a patella most frequently becomes displaced between 20 and 50 degrees of motion, by keeping a patella aligned while in motion about the medial groove allows for quicker and more efficient healing of torn collagen fibers.

Advantageously, the relationship created by the hook and pile adaptations of the straps 180, along with the hook and pile pads 210 and 220 making up the outside of compression member 200 acts to further embrace the patella. Greater strength connections are provided by the hook and pile connections between straps 180 and compression member 200 as tension is increased along the connection between compression member 200 and the straps. When hook and pile connections are pulled in tension, greater strength is provided because more resistance occurs along the hook and pile connections. A greater amount of hooks come into contact with a greater amount of pile fasteners, in turn strengthening the overall connection. As a user bends his or her legs, straps 180 elastically pull in tension against compression member 200. Since a portion of the straps 180 are made of elastic, the amount of tension is exerted on compression member 200 is offset, rather than directly correlating the corresponding forces directly to the patella. Since the straps 180 have elastic properties, when sufficient compression has been supplied to a patella, an overabundance of tension is not exerted against the patella, while providing added strength along the hook and pile connections of compression member 200.

It is evident by the foregoing description that the invention of the subject application has significant benefits and advantages, in particular: (1) the rigid shell frame provides a solid mounting point which allows grabbing of both bone and muscle, (2) the compression member is designed to have a higher angular pull when the knee is bent between 20 degrees and 50 degrees, (3), Y-shaped straps spiral, starting at the midpoint, making one full turn, going through a slot, and attaching to the same side with a quick release buckle, (4) Y-shaped pad having a plastic plate and air bladder disposed therein, (5) the plastic plate acts like a lever, supplying variable tension in a linear direction, (6) a double stretch elastic strap provides better support, and (7) a 10 degree hinge offset between femur and tibia.

The particular embodiments disclosed above are illustrative only, as the invention may be modified and practiced in different but equivalent manners apparent to those skilled in the art having the benefit of the teachings herein. It is therefore evident that the particular embodiments disclosed above may be altered or modified, and all such variations are considered within the scope and spirit of the invention. Accordingly, the protection sought herein is as set forth in the description. It is apparent that an invention with significant advantages has been described and illustrated. Although the present invention is shown in a limited number of forms, it is not limited to just these forms, but is amenable to various changes and modifications without departing from the spirit thereof.

What is claimed is:

1. A patella brace, comprising:
   a rigid frame, comprising:
      a first rigid shell;
      a second rigid shell; and
      a hinge assembly operably coupling the first rigid shell to the second rigid shell, thereby allowing translation;
   a compression member extending around a portion of a knee joint;
   wherein the compression member is adapted to restrain the knee joint while the rigid frame translates about the hinge assembly;
   a first elastic strap securely coupling the first rigid shell and the compression member to a leg; and
   a second elastic strap securely coupling the second rigid shell and the compression member to the leg;
   wherein the compression member is adapted to have a higher angular pull when the knee joint is bent.

2. The patella brace according to claim 1, wherein the rigid shells are anatomically contoured to securely couple about a femur and a tibia to prevent rolling of the patella brace.

3. The patella brace according to claim 2, wherein the hinge assembly is offset by 10 degrees between the femur and the tibia.

4. The patella brace according to claim 1, wherein the compression member is adapted to have the higher angular pull when translated between 20 degrees and 50 degrees.

5. The patella brace according to claim 1, wherein the rigid shells have opposing sets of mate points formed about the ends of the rigid shells.

6. The patella brace according to claim 5, wherein the opposing sets of mate points are gears.

7. The patella brace according to claim 1, further comprising:
   a buckle disposed on each rigid shell for releasably coupling a strap.

8. The patella brace according to claim 1, wherein the first elastic strap, the second elastic strap, and the compression member are operably secured on the same side of the patella brace.

9. The patella brace according to claim 1, further comprising:
   a cushion removably coupled to the compression member for restraining a joint.

10. The patella brace according to claim 1, wherein the compression member includes at least one pad.

11. The patella brace according to claim 1, wherein the compression member comprises:
   a bladder disposed within the compression member for applying pressure to a side of the knee joint.

12. The patella brace according to claim 11, further comprising:
   a nozzle in fluid communication with the bladder for expanding and collapsing the bladder.

13. The patella brace according to claim 1, wherein the compression member comprises:
   a flexible plate disposed between the two pads.

14. The patella brace according to claim 13, wherein the flexible plate exerts pressure on the bladder.

15. A method of stabilizing a joint injury, comprising:
   coupling a first rigid shells and a second rigid shell about the contours of at least one appendage;
   embracing a joint with a compression member;
   securing the compression member with a first strap attached to the first rigid shell;
   securing the compression member with a second strap attached to the second rigid shell;
   adjusting pressure within the compression member; and
   increasing an angular pull with the compression member as the two rigid shells bend with relation to each other;
   wherein the two rigid members remain in an affixed position as the appendage translates about the compression member.

16. The method according to claim 15, further comprising:
   restraining the joint as the appendage translates between 20 and 50 degrees.

17. The method according to claim 15, wherein the joint is a patella.

* * * * *